(12) United States Patent
Harvey et al.

(10) Patent No.: US 7,412,278 B2
(45) Date of Patent: Aug. 12, 2008

(54) METHOD FOR SIMULATION OF AN ELECTRIC STIMULATION IN AN MR IMAGING SYSTEM

(75) Inventors: Paul Royston Harvey, Eindhoven (NL); Jouke Smink, Eindhoven (NL); Gerardus Nerius Peeren, Eindhoven (NL); Jacob Anne Den Boer, Son (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 297 days.

(21) Appl. No.: 10/554,339

(22) PCT Filed: Apr. 22, 2004

(86) PCT No.: PCT/IB2004/050489

§ 371 (c)(1),
(2), (4) Date: Oct. 24, 2005

(87) PCT Pub. No.: WO2004/093680

PCT Pub. Date: Nov. 4, 2004

(65) Prior Publication Data

US 2007/0010737 A1    Jan. 11, 2007

(30) Foreign Application Priority Data

Apr. 24, 2003  (EP) .................................. 03101145

(51) Int. Cl.
    *A61B 5/05*   (2006.01)
(52) U.S. Cl. ...................... 600/416; 600/410; 324/307; 324/318

(58) Field of Classification Search .................. 324/318; 600/407–410, 416
See application file for complete search history.

(56) References Cited

U.S. PATENT DOCUMENTS

| 6,169,403 B1 * | 1/2001 | Hebrank et al. ............. 324/318 |
| 2001/0020120 A1 | 9/2001 | Brand | |

OTHER PUBLICATIONS

Bowtell, R., et al.; Analytic Calculations of the E-Fields Induced by Time-Varying Magnetic Fields; 2000; MRM; 44:782-790.*
Chronik, B.A., et al.; A Comparison Between Human Magnetostimulation Thresholds in Whole-Body and Head/Neck Gradient Coils; 2001; MRM; 46:386-394.*

(Continued)

*Primary Examiner*—Brian L. Casler
*Assistant Examiner*—John F Ramirez (57) ABSTRACT

A novel method is described for simulation of an electric stimulation of the nerve system subject to the rate of change of gradient fields. A gradient signal is filtered and a stimulation signal is derived, which is compared with a predetermined stimulation threshold value. An indicator signal is generated if the threshold value is exceeded. Therefore the time dependent and spatially dependent electric fields as defined by the scanning sequence and the gradient coil properties are calculated. A vector combination of said calculated electric field components from each gradient coil axis is performed, which results in a temporal diagram of the total electric field at various spatial locations within the gradient coil. The stimulation probability at each location from said temporal diagram and said stimulation signal is then calculated, and said stimulation probability is compared with the stimulation threshold value at each location within the gradient coil.

16 Claims, 13 Drawing Sheets

OTHER PUBLICATIONS

Dawson, T.W., et al.; High-Resolution Organ Dosimetry for Human Exposure to Low-Frequency Magnetic Fields; 1998; IEEE; 34(3)708-718.*

Trevor W. Dawson, and Maria A. Stuehly. "High-Resolution Organ Dosimetry for Human Exposure to Low-Frequency Magnetic Fields". IEEE Transactions on Maonetics, vol. 34, No. 3, May 1998.*

Boer, J.A.D., et al.; Generalization to complex stimulus shape of the nerve stimulation thresholds based on existing knowledge; 1999; Proc. Int. Soc. MRM; 7:108.

Budinger, T.F., et al.; Physiological Effects of Fast Oscillating Magnetic Field Gradients; 1991; J. Comp. Assist. Tomography; 15:909-914.

Harvey, P.R., et al.; Avoiding Peripheral Nerve Stimulation: Gradient Waveform Criteria for Optimum Resolution; 1994; MRM 32:236-241.

Hebrank, F.X., et al.; SAFE-Model-A New Method for Predicting Peripheral Nerve Stimulations in MRI; 2000; ISMRM; p. 2007.

Irnich, W., et al.; Magnetostimulation in MRI; 1995; MRM; 33:619-623.

Mansfield, P., et al.; Limits to Neural Stimulation in Echo-Planar Imaging; 1993; MRM; 29:746-758.

Reilly, J.P., et al.; Electrical Stimulation and Electropathology; 1992; Cambridge U. Press; pp. 213-217; pp. 274-280.

* cited by examiner

METHOD FOR SIMULATION OF AN ELECTRIC STIMULATION IN AN MR IMAGING SYSTEM

BACKGROUND

The following relates to methods, apparatuses, and computer program products related to simulation of an electric stimulation of the nerve system in a magnetic resonance (MR) imaging system.

BRIEF SUMMARY

Modern MRI systems utilize high gradient amplitudes and slew rates. When the rate of change (dB/dt) of the magnetic field gradients exceed a specific threshold, the patient experiences peripheral nerve stimulation (PNS). PNS is an undesirable effect and the maximum rate of change of the magnetic field gradients used in an MRI system is regulated by the IEC and FDA. In specific examples it is generally possible to predict when PNS will occur by equating the rate of change of the magnetic field gradient to the electric field (E) that is generated inside the human body as a result of Maxwells equations. A simple model of the temporal resonse of the human nerve to this E-field yields a reasonable prediction of PNS when only simple waveforms are considered. Such simple approaches generally fail when any of the following conditions are met:
- the gradient waveforms are discontinuous and not bipolar,
- more than one gradient axis is used simultaneously,
- the patient is placed at different positions with respect to the gradient coil,
- the gradient coil design varies from system to system.

It is general practise, on a clinical MRI system, to use the simple and conservative model to predict PNS. It is then often the case that the scan performance is limited unneccessarily due to the conservative (worst case) nature of the models used. In recent years, some effort has been made to realize more accurate and flexible models.

Basically the following is known: At the nerve end, an electric field E parallel to the nerve can cause an ion current through the nerve membrane (cf. J. P. Reilly, Electrical Stimulation and Electro-pathology, Cambridge University Press, 1992, pp. 213-217 and pp. 27-280). In a region where the nerve is continuous, the ion current is driven by the first derivative of E. The ionic charge that is built up, can become large enough to create an avalanche, corresponding to nerve excitation. The avalanche propagates along the nerve to the next node etcetera. At long excitation duration, the estimated required intra-patient value of E is 6 V/m (at the nerve end). For shorter excitations, the required field strength increases and the characteristic time involved is about 0.1-0.4 ms. Irnich points out that the situation is not equivalent to an RC circuit; instead, the relation between stimulus duration $\tau$ and threshold stimulus th is hyperbolic (cf. W. Irnich, F. Schmitt, Magnetostimulation in MRI, Mag. Res. Med., 33: p. 619-623, 1995). The long duration limit value of stimulus is called the rheobase rb and the characteristic time is called the chronaxie ch. In formula:

$$th(\tau) = rb\left(1 + \frac{ch}{\tau}\right) \quad (1)$$

The Reilly threshold model and the comments of Irnich are based on experimental work with single electrically induced stimuli. Such stimuli are quite different from the typical repeated stimulus generated by the gradient waveform in the MR system. Nevertheless, the Reilly threshold model can be applied to interpret experimentally observed PNS in MR systems. Early work of Budinger (T. F. Budinger et. al., Physiological effects of fasi oscillating magnetic field gradients, JCAT 1991; 15, p. 909-914), Mansfield (P. Mansfield, P. R. Harvey, Limits to Neural Stimulation in EPI, Mag. Res. Med. 1993; 29, p. 746-758) and Harvey (P. R. Harvey, P. Mansfield, Avoiding peripheral nerve stimulation: gradient waveform criteria for optimum resolution in EPI, Mag. Res. Med. 1993, 32, p. 236-241) illustrate the Reilly model.

It is further supposed in U.S. Pat. No. 6,169,403, on the basis of the dB/dt model (Irnich), that the stimulations caused by an external electric field and the relay (transmission) thereof in the nervous system are approximately described by the filtering of the differentiated gradient signal $G_{diff}(t)$ with a first filtering function $f_{F1}(t)$ and by filtering of its rectified portion Abs ($G_{diff}(t)$) with a second filtering function $f_{F2}(t)$. The gradient signals G(t) are measured by the electric current through the related gradient coil. The first filtering function $f_{F1}(t)$ describes herein the excitation of the action potential on the presynaptic side, which causes chemical messenger substances to be diffused out, and is processed in a first low pass filter stage. These messenger substances are absorbed on the postsynaptic side, i.e. in nerve cells downstream, where they trigger a further action potential. The excitation of the action potential at the postsynaptic side is described by the filtering function $f_{F2}(t)$. Since the original polarity of the excitation is no longer contained in the action potential at the postsynaptic side, only the rectified portion of the differentiated gradient signal $G_{diff}(t)$, which is designated Abs ($G_{diff}(t)$), is processed in a second low pass filter stage. Thus, the aborting of the executed measuring sequence occurs given the crossing of a threshold value in an online monitoring. This crossing of the threshold value is signaled prior to the execution of the measuring sequence in a look-ahead monitoring.

To account for the discontinuous nature of the generally used waveforms, the concept of convolution of the gradient waveform with the temporal response of the nerve was introduced (cf. J. A. den Boer, Generalization to complex shape of the nerve stimulation threshold based on existing knowledge of its relation to stimulus duration for rectangular. stimuli, ISMRM 1999, p. 108). In this model a simple representation of the temporal response of the nerve is used which does not account accurately for changes in response as a result of repeated waveforms. This model explains the waveform dependency of the PNS threshold, but not the observation by Budinger (supra) and Hebrank (F. Hebrank, M. Gebhardt, SAFE model-a new method for predicting PNS in MRI. ISMRM 2000, p. 2007), who showed that the threshold for a single bipolar waveform gradually decreases when the waveform is repeated more and more often. For a periodic waveform with ramp times of 0.4 ms, the final threshold level is reached after about 10 ms.

The present invention has the aim to provide a more accurate model of the stimulation of peripheral nerves in order to optimize the threshold settings in the MR system.

BRIEF DESCRIPTION OF THE DRAWINGS

Further advantages are disclosed in the following description in which an exemplified embodiment of the invention is described with respect to the accompanying drawings.

FIG. 1 a diagram of the spatio-temporal model for PNS prediction according to the present invention, FIG. 2 a rectifying filter with weight dependent stimuli of opposite polarity, FIG. 3 another rectifying filter with weight dependent stimuli of single polarity, FIG. 4 the combined filter according to the present invention, FIG. 5 a diagram of the stimulation threshold versus gradient rise time, FIG. 6 a diagram of the stimulation threshold as a function of the stimulation length, and FIG. 7 a diagram of the stimulation threshold versus the number of gradient signals.

DETAILED DESCRIPTION OF THE PREFERRED EMBODIMENTS

Specific numbers dedicated to elements defined with respect to a particular figure will be used consistently in all figures if not mentioned otherwise.

Since a more general model for the temporal nature of the nerve behavior is established, the next challenge is to incorporate spatial information of the time varying E-fields into the model. When the exact temporal and spatial nature of the time dependent gradient and E-fields generated during an MRI scan is taken in consideration, scan parameter optimization, and system operation, closer to the limits of PNS can be enabled. This is the basis of the present invention.

Figures 1, 13:
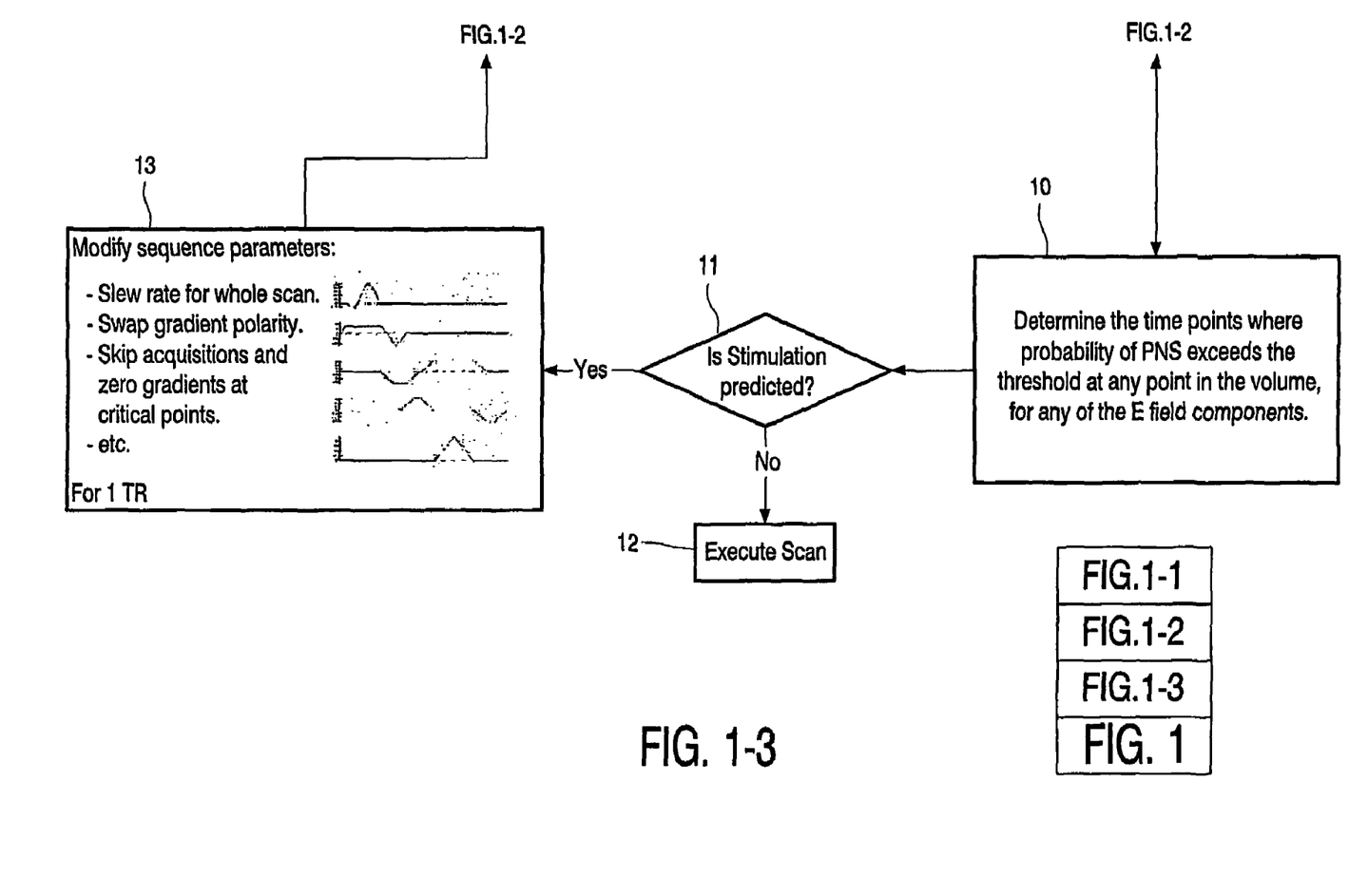
Figure 4:
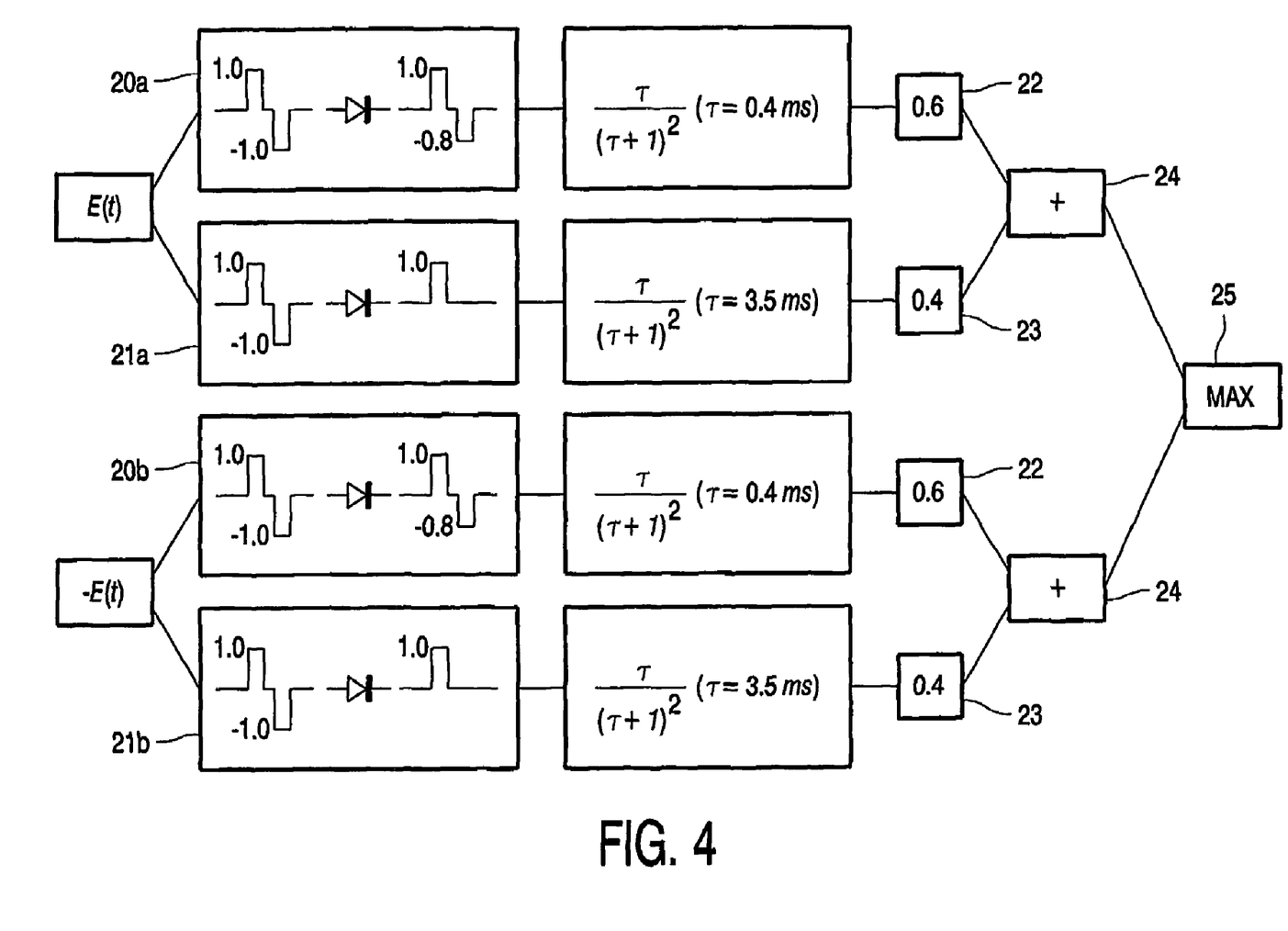

According to the diagram in FIG. 1 a more accurate temporal model for the peripheral nerve response to time varying magnetic (B) and electric (E) fields can be presented in a flow diagram of the sequences of events required to determine if PNS will occur with a particular scanning method. As such it describes the functionality of the software code that is required to implement such a check on an MRI system. Firstly the specific MR imaging method is chosen by the user and the parameters are defined. In a preliminary approach prior to the beginning of magnetic resonance imaging, the explicit knowledge of the magnetic design or properties of the gradient coils GC1 and GC2 and the actual measured parameters of the specific gradient coil as shown in box 1 are implemented in decision step 2. Especially, the sequence parameters such as slice angulation, number of slices, gradient coil signal etc. for a period of a single repeating cycle TR are provided in box 1. In next step 3 the differentiated gradient signal is filtered. Thereafter the time dependent and spatially dependent E-fields for each gradient axis ($G_x$, $G_y$ and $G_z$) as defined by the scanning sequence and the gradient coil properties over a single cycle TR (either in vacuum or in a cylindrical body model) are calculated in step 4. Optionally in step 5, a 3D mask based upon a preliminary or scout scan can be obtained, in order to determine exactly where and how the patient is positioned inside the imaging volume. With such a spatial masking of the E-field space the orientation and position of the body of the patient within the gradient coil can be identified and the number of calculations can be reduced. In following step 6 the vector sum of the E-field components from each gradient coil axis over a single cycle TR is calculated, which results in a time dependent description of the overall or net E-field at various spatial locations within the gradient coil. In step 7 the result of the vector sum is extrapolated over N times the repetition time TR and the number M of slices. Therein the encoding steps and the slice angulations are included. Optionally in step 8, additional information can be included, that relates to patient size and weight (which can be derived from the RF power calibration) in order to fine tune the threshold settings of the stimulation model on a patient by patient basis. In step 9 the so determined spatio-temporal E-field components are inputted into the stimulation prediction model:

$$\bar{E} = \frac{1}{\tau} \cdot \int_\tau E(t)\,dt \geq E_r \cdot \left(1 + \frac{\tau_0}{\tau}\right) \quad (2)$$

wherein $\tau$ the stimulus duration and $\tau_0$ the characteristic time or chronaxie (see FIG. 4).

The prediction or stimulation probability is evaluated for each $E_x(t)$, $E_y(t)$ and $E_z(t)$ independently. The nerve response is calculated as a function of space and time to yield three spatio-temporal PNS stimulation probability trajectories. In step 10 the time points are determined where the probability of PNS exceeds the threshold at any point in the volume, for any of the E-field components. If in decision step 11 stimulation is not predicted then the scan can be executed—step 12, otherwise the sequence parameters will be modified in step 13 and the modified parameters are implemented in step 3 for another iteration. The modifications concerns the slew rate of the whole scan, the swap of the gradient polarity, skipping acquisitions and putting gradients to zero at critical points, etc. Since the exact point in time, of nerve stimulation, can be identified in advance, the option exists to modify the sequence in its entirety, or just around the time point of stimulation, so as to prevent the occurrence of nerve stimulation.

The proposed novel model of PNS extends the concept of convolution of the induced current, or E-field, waveform and the nerve response. The following properties of the nerve have been observed and documented:

The nerve responds in a non-linear way depending upon the relative polarity, and timing, of successive stimuli.

Following activation of the nerve, there is a refractory period (recovery time) during which the nerve can not be stimulated any more.

Repeated stimulation leads to a de-sensitization of the nerve (or at least the perception).

From the above mentioned observations it is concluded that the nerve response to a train of unipolar stimuli is different to a train of bi-polar stimuli. It is known that a negative going stimulus can only cancel the effect of a positive going stimulus under very specific conditions. In general, an equal amplitude negative stimulus, following a positive stimulus, will not prevent nerve excitation. Therefore, it is concluded that the sensitivity of the nerve to opposite polarity stimuli is modified by the effect of the previous stimuli (ionic concentration is not reversed completely).

Figure 2:
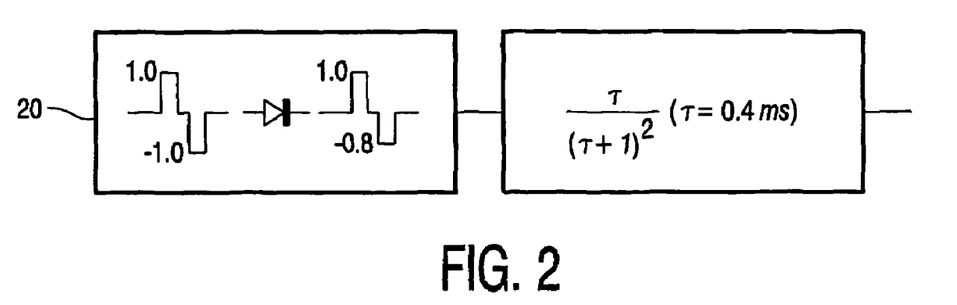

To model this behavior, a filter 20 is utilized which weights differently stimuli of opposite polarity as is shown in FIG. 2. The partially rectifying filter 20 also accounts for the nerve recovery time mechanism which is also resulting from non-immediate reversal of ionic concentration. Even partial, but incomplete, excitation can change the sensitivity of the nerve to the stimuli that will follow. The filter 20 accounts for that mechanism. The output, following the filter, represents some measure of the potential for the nerve to be stimulated. When the input is the E-field, then the output represents the fraction of that E-field that can be compared with the required threshold for stimulation. When the ratio is equal to 1, then stimulation occurs.

The observation that repeated stimuli leads to a lower threshold can be modeled by making the stimulation threshold dependent on the total length of the stimuli. For a complex MR sequence this implies that the whole waveform is taken across many repetition times TR. It is reasoned that final stimulation ultimately depends upon the polarity of the initial stimulus since the sensitivity to subsequent stimuli of opposite polarity is reduced as described above.

Figure 3:
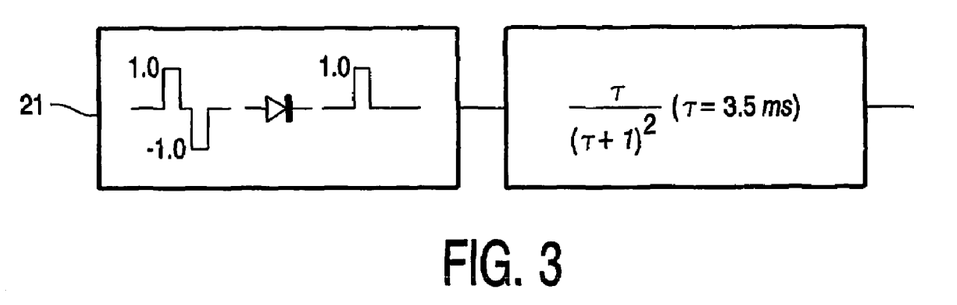

The second filter 21 as shown in FIG. 3 operates over a longer time scale and considers only the stimuli of a single polarity. The output of this filter 21 behaves like a DC addition to the stimulus potential. This depends upon the longer time scale duration of the stimulus waveform. There is also an element of bias towards the initial polarity of the stimulus. When the input is the E-field waveform, the output represents a fraction of this E-field that must be added to the output of the first filter 20, thereby making the possibility to reach the stimulation threshold more likely. The outputs from the two filters 20 and 21 are therefore summed.

An additional measure is required because it is not known which polarity of E-field the nerve inside a human body is exposed to. This depends upon many factors, not least the location of the nerve with respect to the gradient coil. Since the model up to now is polarity sensitive, it is necessary to account for the fact that the initial polarity cannot easily be known. This is done by simply calculating the inverse of the input waveform before applying the two filters 20 and 21. The summed output is then compared with the output calculated using the original waveform. The final output is whichever is the maximum of both models as a function of time.

FIG. 4 illustrates the model in its entirety. As mentioned above, it is preferable to normalize the final output of the model to a calibrated threshold such that an output below 1.0 indicates no stimulation and an output above 1.0 indicates stimulation. The differentiated waveform g(t) of the gradient coil is split in two parts. In the upper filter stage 20*a*, the negative part of the waveform g(t) is scaled with a factor 0.8. In the lower filter stage 21*a* only a single polarity is considered. Thereafter the output signals of both filters 20*a* and 21*a* are multiplied with a weighting factor $\alpha_1$ and $\alpha_2$ in multipliers 22 and 23 respectively, whereas $\alpha_1+\alpha_2=1$. In this case $\alpha_1=0.6$ and $\alpha_2=0.4$. Thereafter, the output signals are summed in adder 24. Since this operation would be sensitive to the polarity of the waveform, the same operation is repeated for the inverse waveform -g(t) in upper filter stage 20*b* and in lower filter stage 21*b*. The maximum of both models obtained in comparator stage 25 is used as output.

In short, the new model has following important properties:
1. Utilization of a more accurate temporal model for nerve response to time varying B- or E-fields.
2. Incorporation of explicit knowledge of the magnetic design of the gradient coils used.
3. Calculation of the time dependent and spatially dependent E-fields as defined by the scanning sequence and the gradient coil properties.
4. Vector combination of the E-field components from each gradient coil axis resulting in a time dependent description of the net E field at various spatial locations within the gradient coil.
5. Calculation of the stimulation probability at each location using the refined temporal model for the nerve response.
6. Utilizing knowledge derived from the effect of patient loading, as determined by the QBC RF power calibration, as a means to determine patient size for the purpose of weighting the stimulation probability for small or large patients and/or different body positions.
7. Identifying the position and time point of likely stimulation and providing a warning to the operator.
8. Optional refinement of the MR pulse sequence as a result of feedback from the predicted stimulation probability.
9. Optional spatial masking of the E-field space using a mask derived from a preview MR image of the body within the gradient coil (to identify body position and reduce the number of calculations).
10. Incorporation of an explicit numerical description of the electrical properties of the human body to aid in accuracy of the E-field determination.
11. The possibility to utilize the model with more than one gradient coil type in the same MR system.
12. Integration of all the above points in a software program which is resident on the computer of an MR system and executed as part of the general execution of each imaging scan.

Experimental Evaluation of the Novel Model

Figure 5:
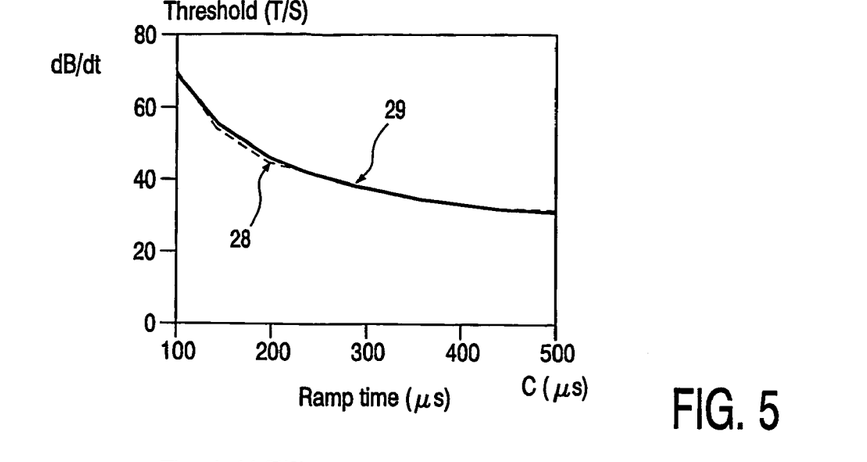
Figure 6:
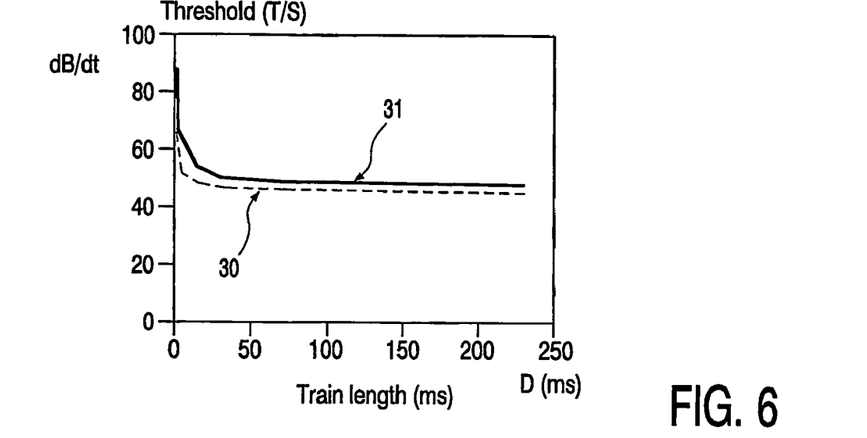

FIG. 5 shows validation of the model according to the present invention against published data by F. Hebrank and M. Gebhardt in ISMRM 2000, p. 2007. The first plot shows the performance comparing stimulation threshold dB/dt in T/sec versus gradient rise time C in μsec. The dashed line 28 is the output from the novel model as presented here. The solid line 29 is the measured Hebrank data. The second graph in FIG. 6 shows the results of the stimulation threshold dB/dt in T/sec as a function of the stimulation length D in msec. The agreement of the calculated data (dashed line 30) with the measured data from Hebrank (solid line 31) is within 10%. Thus the here presented novel model is at least as accurate as the Hebrank model. However, the trend behavior is better with the novel model.

Figure 7:
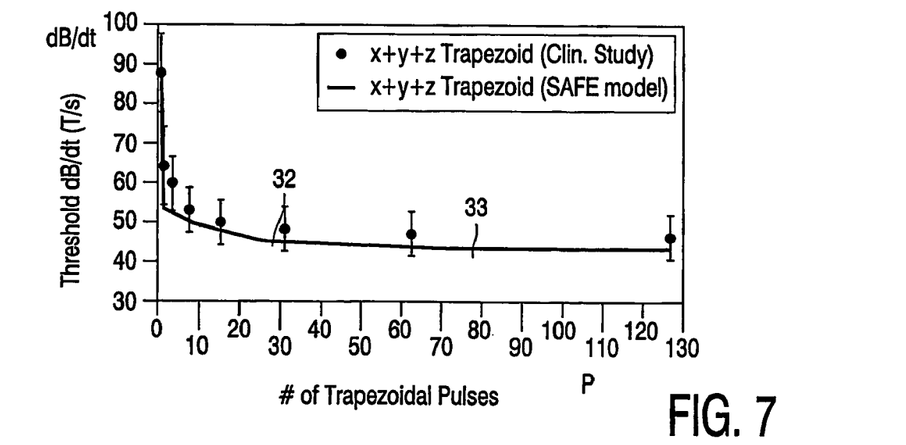

FIG. 7 shows the published Hebrank data and the accuracy of the SAFE model for comparison with FIG. 6. The solid dots 32 present the data of a clinical study and the solid line 33 presents the calculated graph according to the SAFE model. At the ordinate again the stimulation threshold dB/dt and at the abscissa the number of trapezoidal pulses P.

Figure 8:
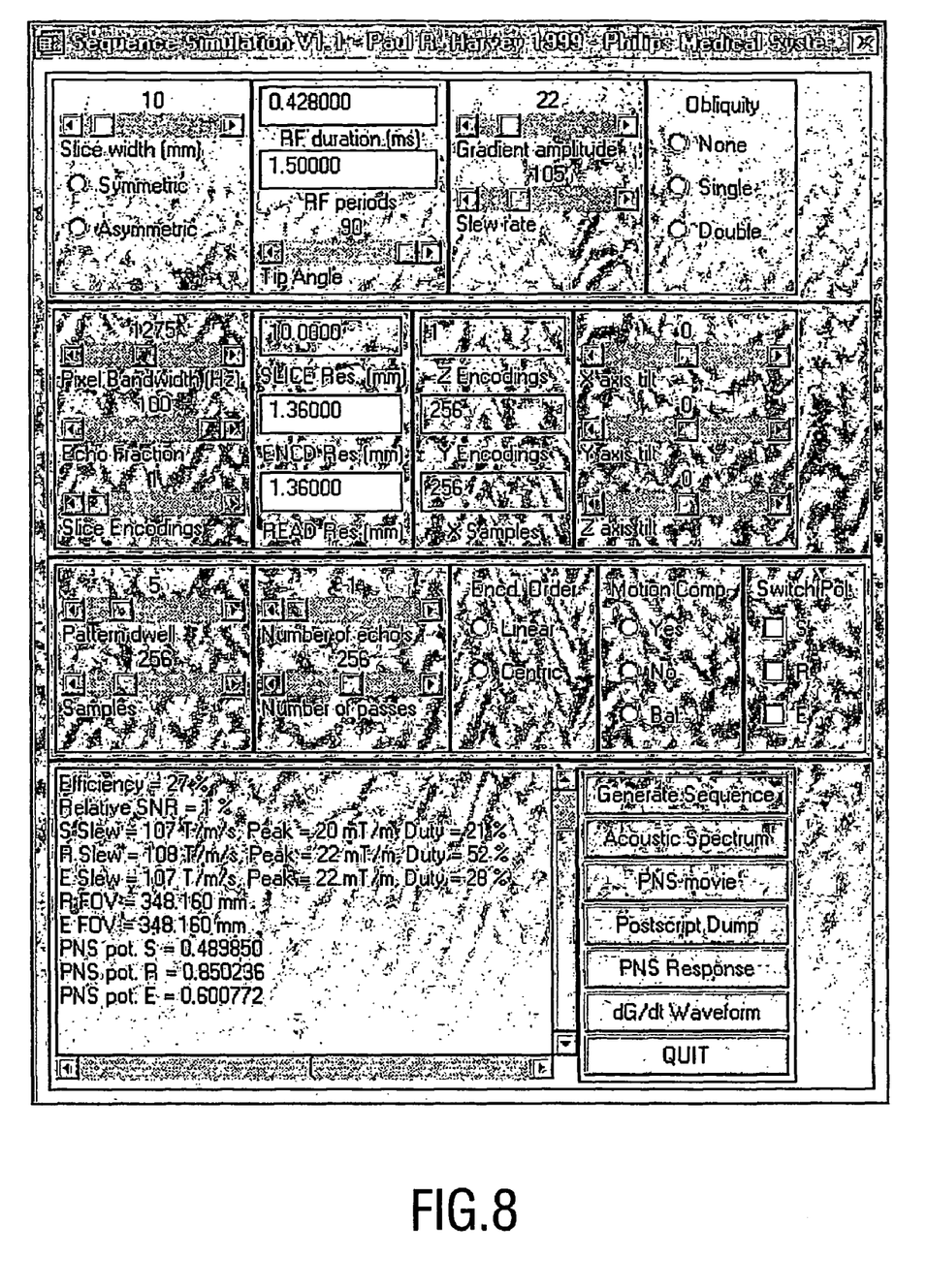
FIG. 8 shows a print-out of the user screen of the console of an MRI apparatus.
Figure 9:
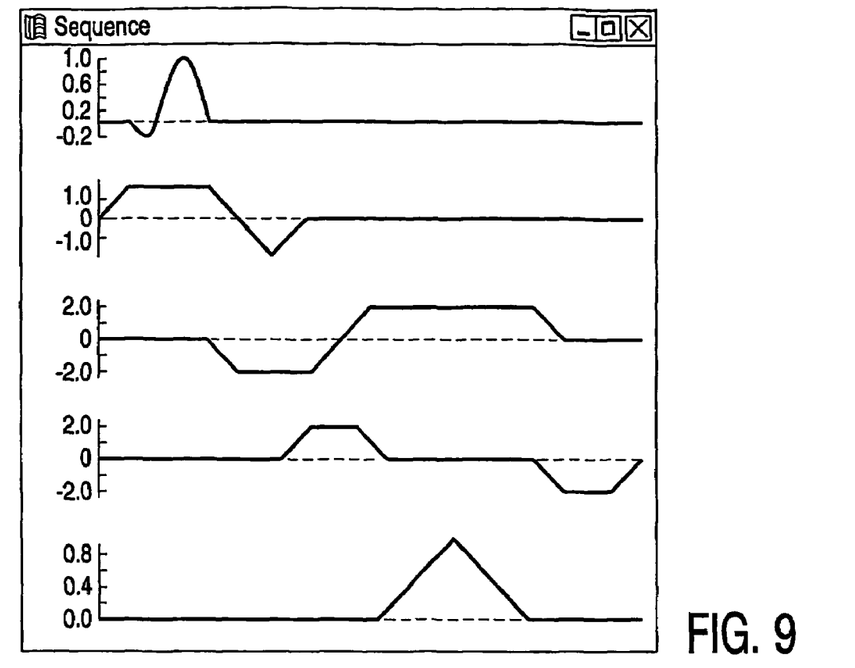
FIG. 9 shows a gradient waveform plot.
Figure 10:
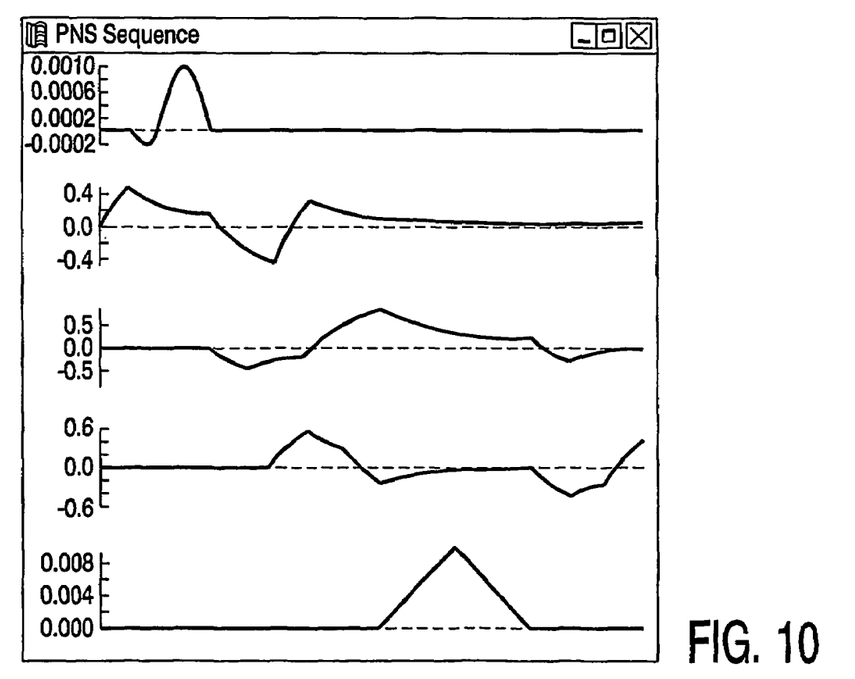
FIG. 10 shows a PNS prediction plot as calculated.

FIG. 8 shows a print-out of the user screen of the console of an MRI apparatus in which the above mentioned novel model have been tested. FIG. 9 shows the gradient waveform plot and FIG. 10 the PNS prediction plot as calculated. The software developed for the novel model performs a real-time MR method optimisation/design for various sequences and hardware parameters. It utilizes the above mentioned convolution method and the novel model of the nerve to predict if peripheral nerve stimulation can occur using the sequence shown under the parameter limitations given. At the moment this prediction is displayed, per axis, in the form of the nerve response to the gradient stimuli. Values below 1.0 are below the threshold and values above 1.0 represent stimulation. The PNS prediction algorithm is "trained" on the Hebrank data and does take into account the longer term effects relating to the number of gradient cycles. The effective length of the gradient coil is in this case 0.45 m as for a typical whole body gradient coil. In this case a simple FFE sequence is shown with gradient amplitude and flew rate limited to 22 mT/m and 105 T/m/s. All three axes are sub-threshold for this single repetition time TR although continuing the prediction to later TR's may show that stimulation will occur. This is implied in the EPI sequence below.

Figure 11:
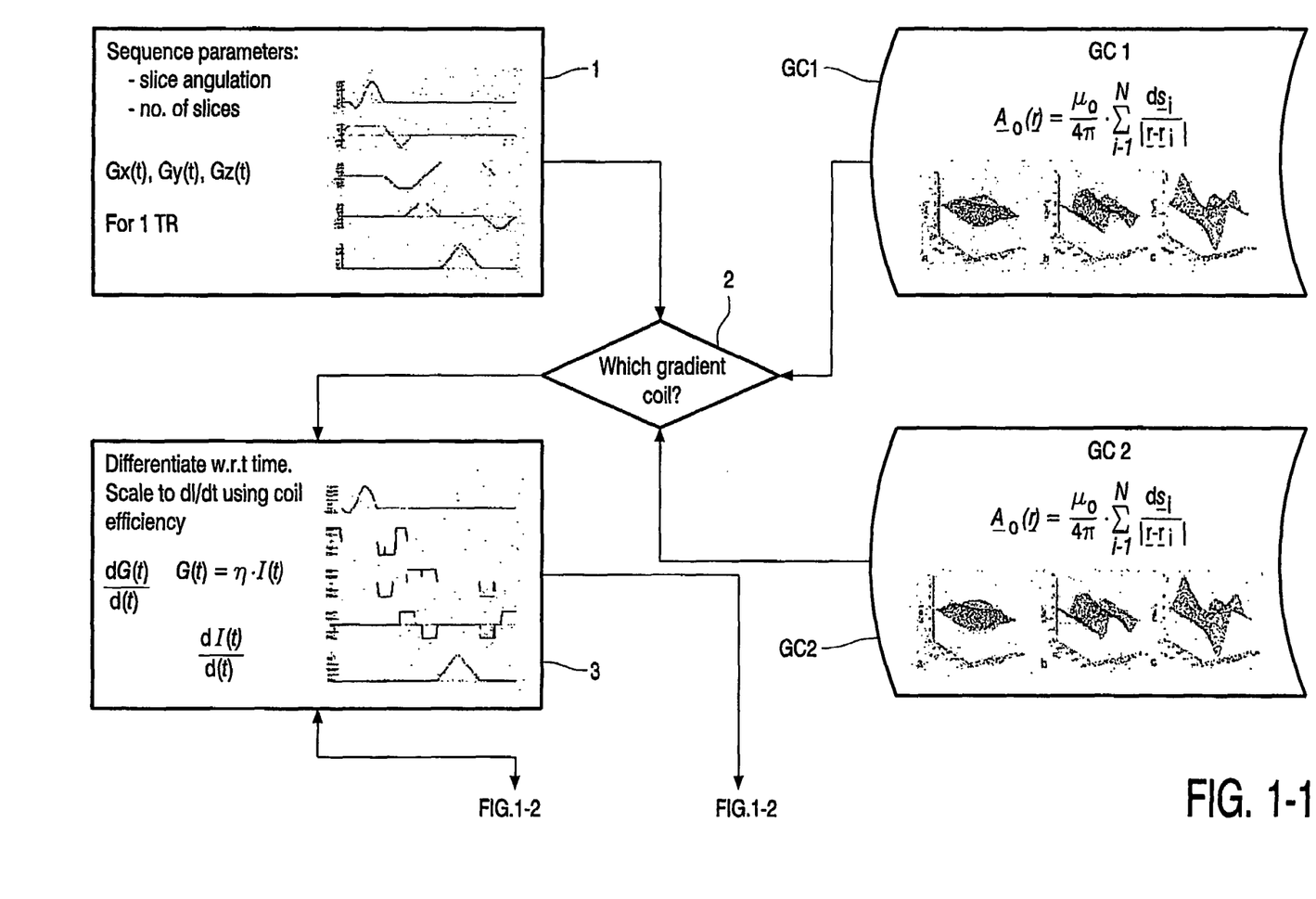
FIG. 11 shows a screen print-out showing the sequence parameters.
Figure 12:
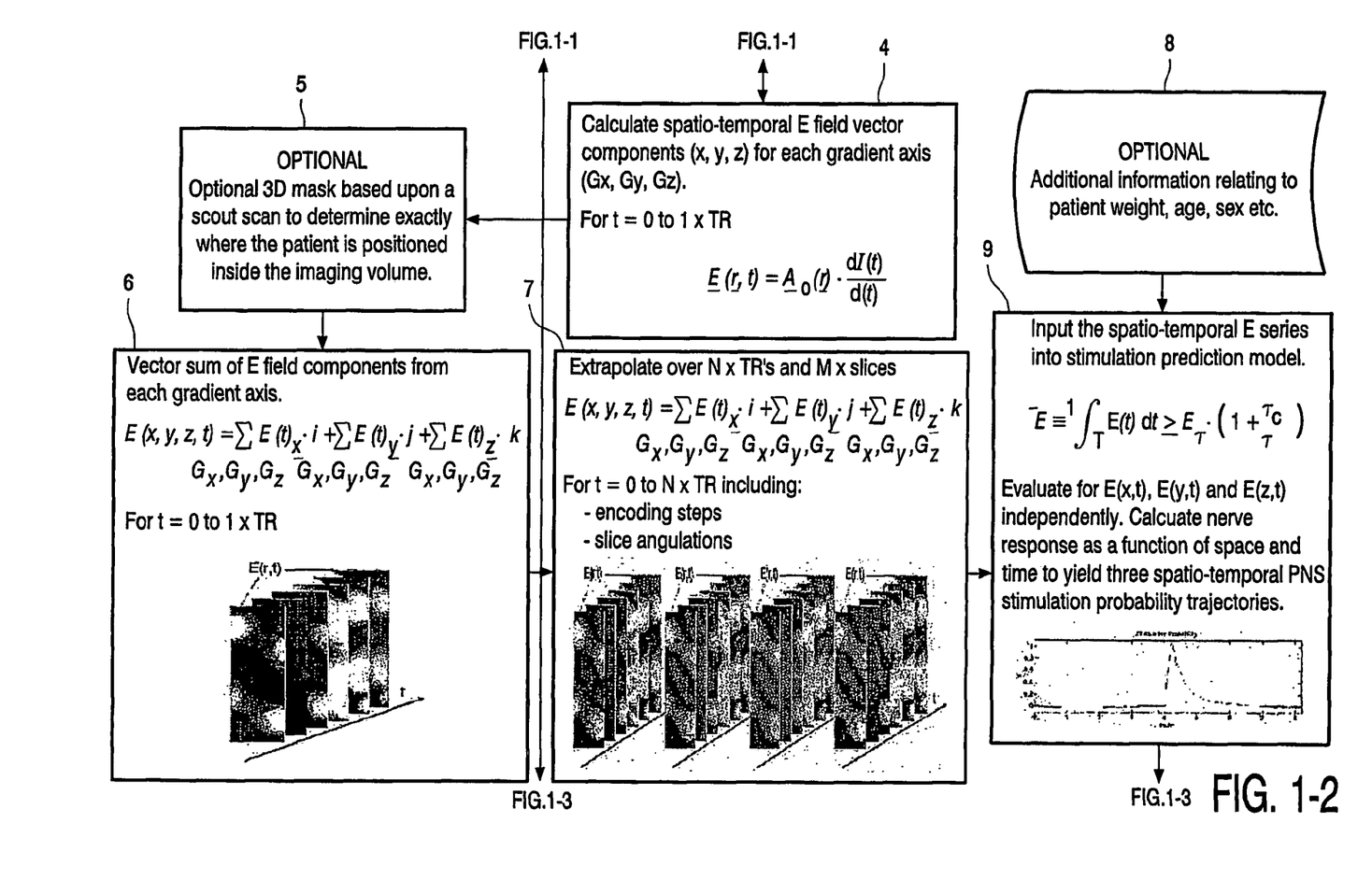
FIG. 12 shows another gradient waveform plot.
Figure 13:
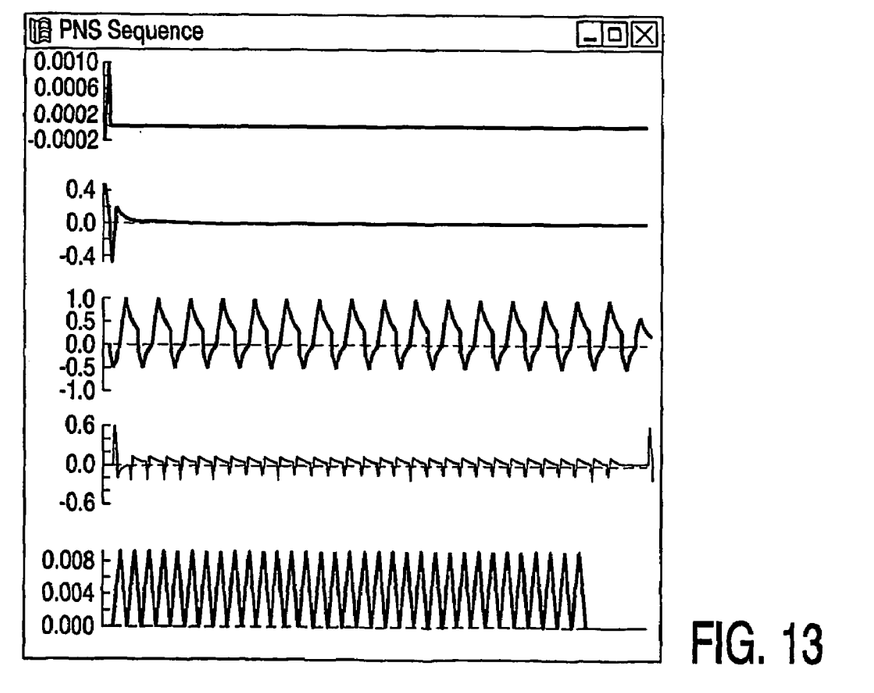
FIG. 13 shows another PNS prediction plot.

In FIG. 11 the screen print-out is showing the sequence parameters for identical sequence parameters (FOV etc.) as in to the previous case above (FIG. 8) except a 32 echo EPI readout is used. In this case the PNS threshold is predicted to be exceeded for the readout (measurement) axis. In this case the software would predict a stimulation. This is consistent with the knowledge that FFE is less likely to produce stimulation than EPI. In FIG. 12 the gradient waveform plot is depicted and in FIG. 13 the PNS prediction plot.

Figure 14:
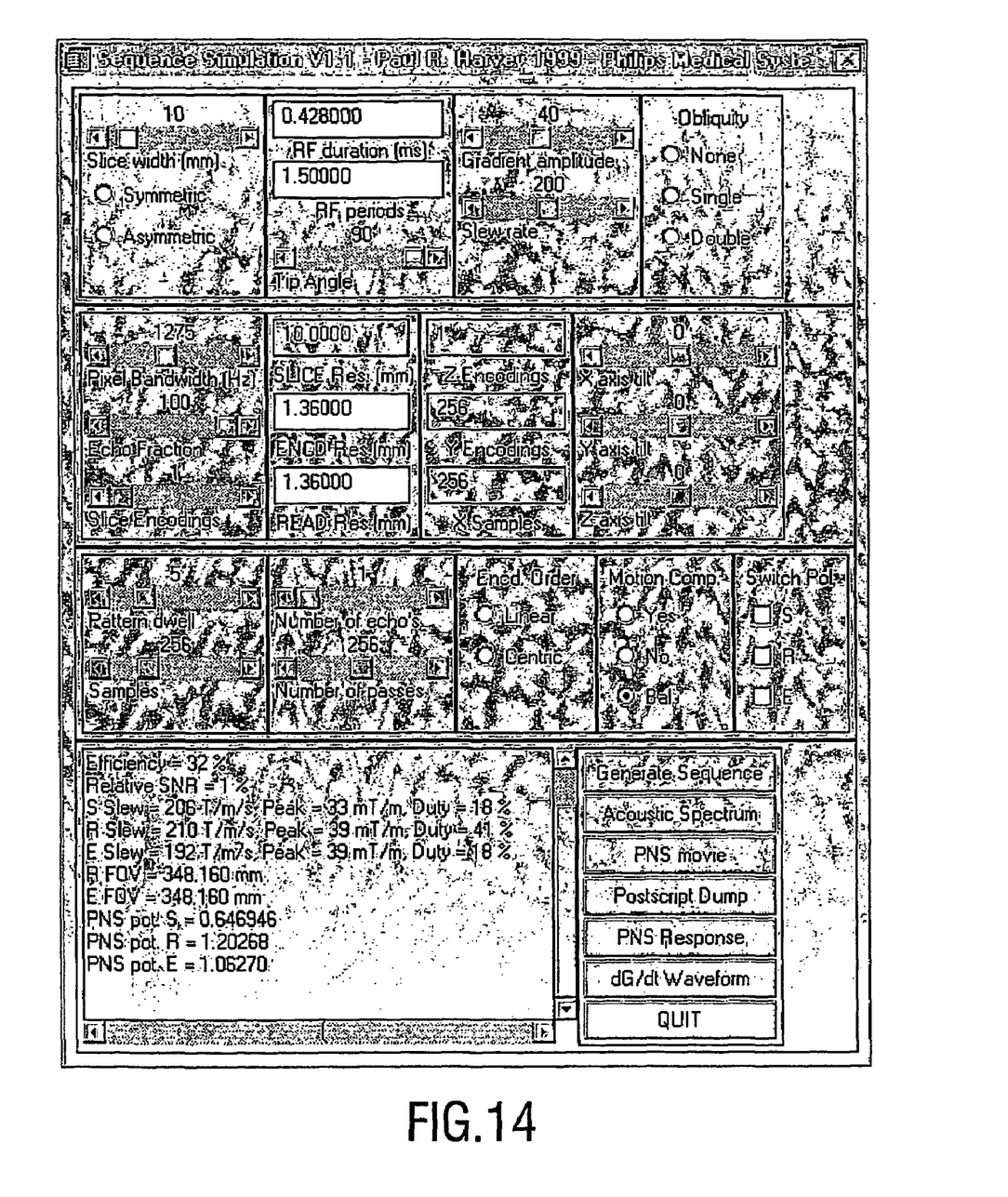
FIG. 14 shows a balanced FFE with higher gradient amplitude.
Figure 15:
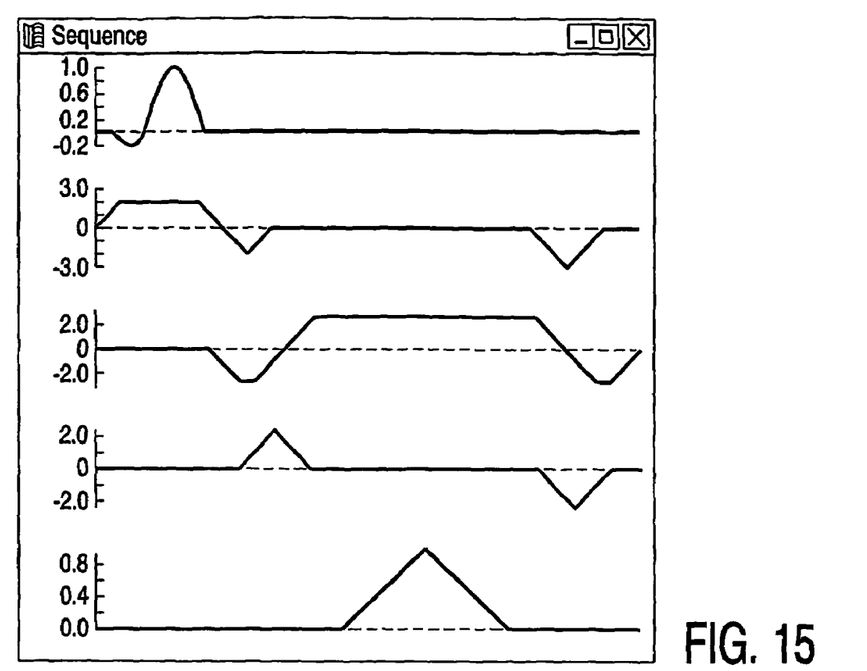
FIG. 15 shows a further gradient waveform plot.
Figure 16:
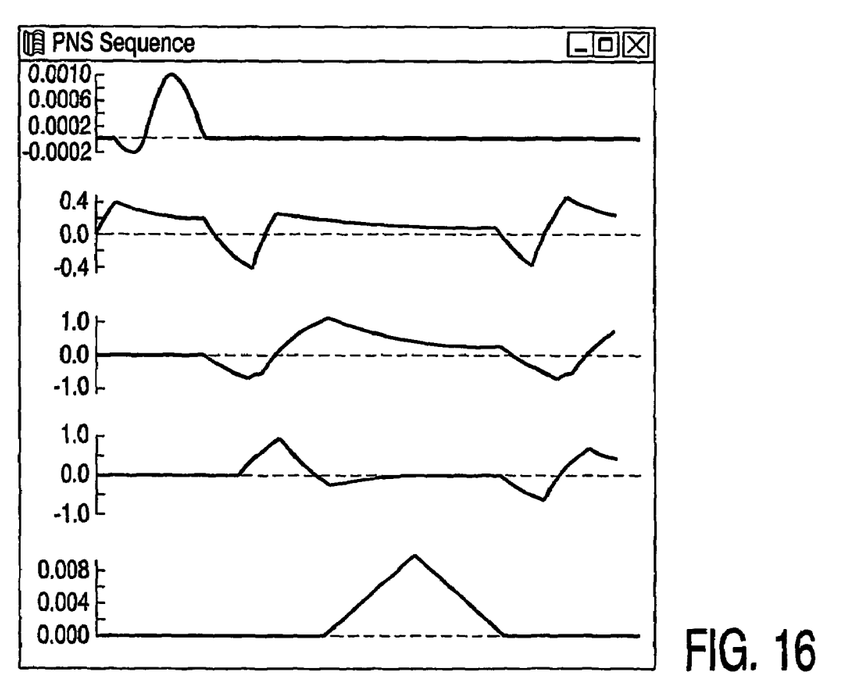
FIG. 16 shows a further PNS prediction plot.

A balanced FFE with higher gradient amplitude is another issue shown in FIG. 14 (screen print-out), FIG. 15 (gradient waveform plot) and FIG. 16 (PNS prediction plot). Here the supra-threshold situation B to FFE and higher gradient performance is investigated. In this example a gradient performance of 40 mT/m and slew rate 200 T/m/s is assumed with a typical whole body gradient coil. Now, for the same image parameters as above, PNS is predicted due to both the preparation axis and the measurement axis.

Figure 17:
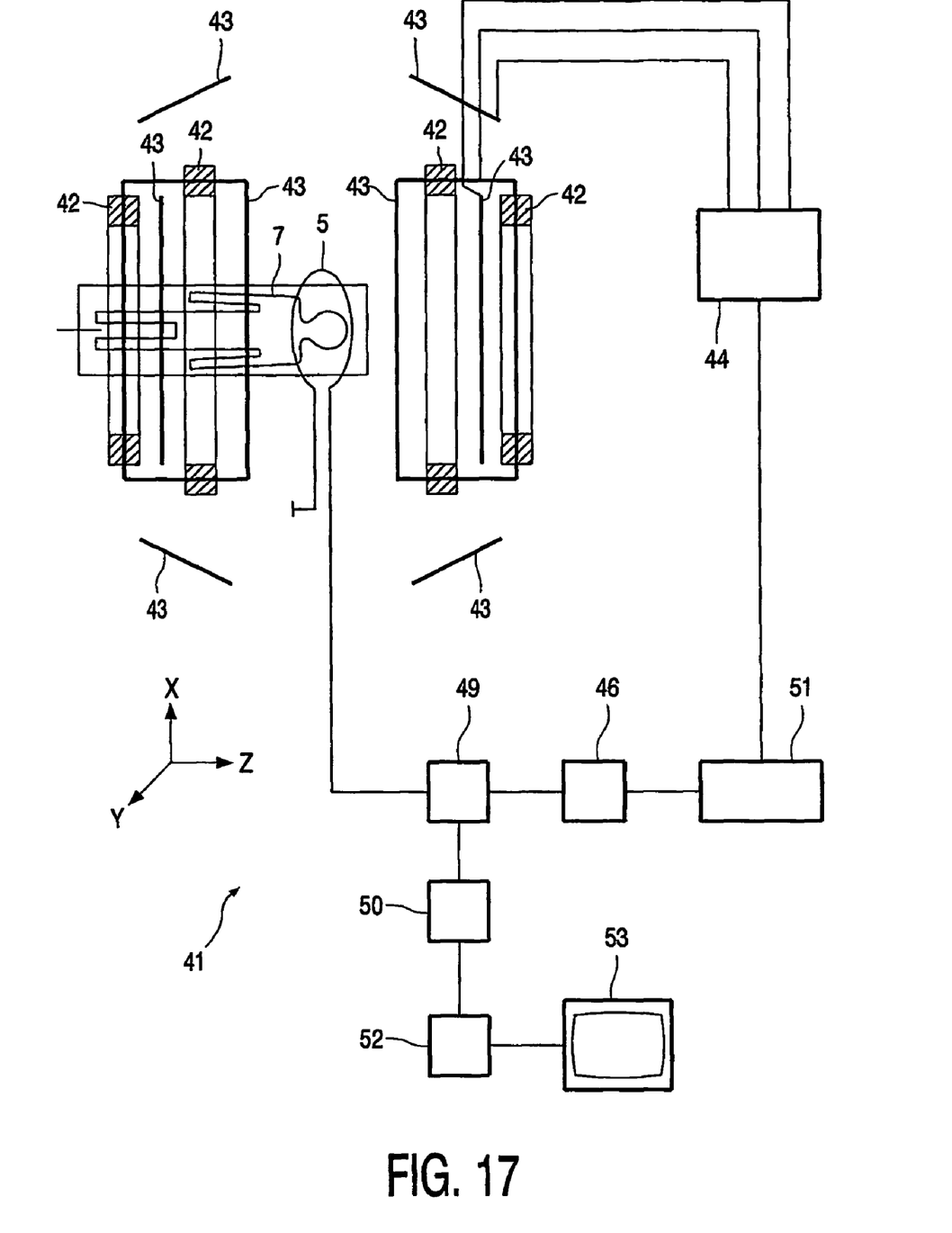
FIG. 17 shows a practical embodiment of an MR device for executing the above-mentioned method for simulation of PNS.

A practical embodiment of an MR device for executing the above mentioned method for simulation of PNS is shown in FIG. 17, which includes a first magnet system 42 for generating a steady magnetic field, and also means for generating additional magnetic fields having a gradient in the X, Y, Z directions, which means are known as gradient coils 43. The Z direction of the co-ordinate system shown corresponds to the direction of the steady magnetic field in the magnet system 42 by convention, which only should be linear. The measuring co-ordinate system x, y, z to be used can be chosen independently of the X, Y, Z system shown in FIG. 17. The gradient coils 43 are fed by a power supply unit 44. An RF transmitter coil 45 serves to generate RF magnetic fields and is connected to an RF transmitter and modulator 46. A receiver coil is used to receive the magnetic resonance signal generated by the RF field in the object 47 to be examined, for example a human or animal body. This coil 45 represents an array of multiple receiver antennae. Furthermore, the magnet system 42 encloses an examination space which is large enough to accommodate a part of the body 47 to be examined. The RF coil 45 is arranged around or on the part of the body 47 to be examined in this examination space. The RF transmitter coil 45 is connected to a signal amplifier and demodulation unit 50 via a transmission/reception circuit 49. The control unit 51 controls the RF transmitter and modulator 46 and the power supply unit 44 so as to generate special pulse sequences which contain RF pulses and gradients. The control unit 51 also controls detection of the MR signal(s), whose phase and amplitude obtained from the demodulation unit 50 are applied to a processing unit 52. The control unit 51 and the respective receiver coils 43 and 45 are equipped with control means to enable switching between their detection pathways on a sub-repetition time basis (i.e. typically less than 10 ms). These means comprise inter alia a current/voltage stabilisation unit to ensure reliable phase behaviour of the antennae, and one or more switches and analogue-to-digital converters in the signal path between coil and processing unit 52. The processing unit 52 processes the presented signal values so as to form an image by transformation. This image can be visualized, for example by means of a monitor 53.

The invention claimed is:

1. A method for simulation of an electric stimulation of a nerve system of a subject to be examined generated by a rate of change of gradient fields generated by one or more gradient coils of a magnetic resonance imaging system, wherein a gradient signal is filtered with a filtering function, a stimulation signal is derived from said filtered gradient signal, and said stimulation signal is compared with a predetermined stimulation threshold value for generating an indicator signal if said threshold value is exceeded, the method comprising:

spatially masking a space of the electric field by a mask derived from a preview MR image of the subject's body within the gradient coil, calculating time dependent and spatially dependent electric fields as defined by a scanning sequence and the gradient coil properties within the mask, vector combining said calculated electric field components from each gradient coil axis resulting in a temporal diagram of the total electric field at various spatial locations within the gradient coil, calculating a stimulation probability at each location from said temporal diagram and said stimulation signal, comparing said stimulation probability with a stimulation threshold value at each location within the gradient coil; and providing a warning of likely stimulation based on the comparing.

2. A method as claimed in claim 1, wherein the gradient signal is differentiated, and the differentiated gradient signal is filtered in a first stage with a first bipolar filter and is parallel filtered in a first unipolar filter, the output signals of both first filters are weighted and the weighted output signals are added.

3. A method as claimed in claim 2, wherein the inverse of the differentiated gradient signal is filtered in parallel in a second filter stage with a second bipolar filter and a parallel second unipolar filter, the output signals of both second filters are weighted and the weighted output signals are added to a second stimulation signal, which is compared with the stimulation signal and the maximum of both stimulation signals is used as output signal for comparing with said threshold value.

4. A method as claimed in claim 2, wherein said first bipolar filter weights differently stimuli of opposite polarity.

5. A method as claimed in claim 1, wherein knowledge of the magnetic design of the gradient coils is incorporated in the calculation.

6. A method as claimed in claim 1, wherein knowledge derived from the effect of patient loading is weighted in the stimulation probability for the size and/or position of the patient.

7. A method as claimed in claim 1, wherein the scanning sequence is refined by feedback of the predicted stimulation probability signal.

8. A method as claimed in claim 1, wherein the time dependent components of the electric field in x-, y- and z-direction are extrapolated over multiple repetition periods and multiple slices.

9. A method as claimed in claim 8, wherein the time points and positions in the volume of the gradient coil are calculated for each component of the electric field independently and each of the predicted stimulation probability is compared with the stimulation threshold value.

10. A magnetic resonance imaging apparatus for obtaining an MR image from a plurality of signals and for simulation of an electric stimulation of a nerve system of a subject to be examined, which stimulation is generated by a rate of change of gradient fields, the simulation including filtering a differentiated gradient signal with a filtering function, deriving a stimulation signal from said filtered gradient signal, and comparing said stimulation signal with a predetermined stimulation threshold value for generating an indicator signal if said threshold value is exceeded, the apparatus comprising:
a main field magnet;
gradient coils;
means for filtering the differentiated gradient signal with a filtering function including a first filter stage with a first bipolar filter for filtering the differentiated gradient signal and a first unipolar filter for parallel filtering said differentiated gradient signal and weighing means, in which both output signals are weighted, and adding means, in which the weighted output signals are added;
means for calculating and vector combining time dependent and spatially dependent electric field components from each gradient coil axis based on gradient signals defined by a scanning sequence and filtered by the filtering means and the gradient coil properties resulting in a temporal diagram of the total electric field at various spatial locations within the gradient coils;
means for calculating a stimulation probability at each location from said temporal diagram and said stimulation signal;
means for comparing said stimulation probability with the stimulation threshold value at each location within the gradient coil and generating an indicator signal if said threshold value is exceeded.

11. A magnetic resonance imaging apparatus as claimed in claim 10, wherein the space of the electric field is spatially masked by a mask derived from a preview MR image of the subject's body within the gradient coil.

12. A magnetic resonance imaging apparatus as claimed in claim 11, wherein the filtering means futher comprises a second parallel filter stage with a second bipolar filter for filtering the inverse differentiated gradient signal during approximately a single repetition time period, with a parallel second unipolar filter for parallel filtering said inverse differentiated gradient signal during approximately ten or more repetition time periods, and weighing means, in which both output signals are weighted, and adding means, in which the weighted output signals are added to form a second stimulation signal, and means for comparing said stimulation signal with said second stimulation signal and means for defining the maximum of the stimulation signal and the second stimulation signal as output signal for comparing with said stimulation threshold value.

13. A magnetic resonance imaging apparatus as claimed in claim 10, wherein said first bipolar filter weights differently stimuli of opposite polarity.

14. A computer program product stored on a computer usable medium for forming an image by a magnetic resonance method including a method for simulation of an electric stimulation of a nerve system of a subject to be examined generated by a rate of change of gradient fields of a gradient coil of a magnetic resonance imaging system, the computer program product comprising a computer readable program storage medium storing instructions executable by a computer to control the execution of a plurality of steps comprising:

filtering a differentiated gradient signal of said gradient coil with a filtering function, the filtering including filtering the differentiated gradient signal in a first stage with a first bipolar filter, parallel filtering said differentiated gradient signal in a first unipolar filter, and weighting the output signals of both first filters and adding the weighted output signals,
deriving a stimulation signal from said filtered gradient signal,
comparing said stimulation signal with a predetermined stimulation threshold value for generating an indicator signal if said threshold value is exceeded,
calculation of time dependent and spatially dependent electric fields as defined by a scanning sequence and the gradient coil properties,
vector combination of said calculated electric field components from each gradient coil axis resulting in a temporal diagram of the total electric field at various spatial locations within the gradient coil,
calculation of a stimulation probability at each location from said temporal diagram and said stimulation signal, and
comparing said stimulation probability with a stimulation threshold value at each location within the gradient coil; and
generating said indicator signal if said threshold value is exceeded at any location within the gradient coil.

15. A computer program as claimed in claim 14, wherein the filtering further includes:
filtering the inverse of the differentiated gradient signal in a second filter stage with a second bipolar filter during approximately a single repetition time period,
parallel filtering said inverse signal with a parallel second unipolar filter during approximately ten or more repetition time periods,
weighing both output signals,
adding the weighted output signals to a second stimulation signal,
comparing said first stimulation signal with said second stimulation signal and
defining the maximum of both stimulation signals as output signal for comparing with said stimulation threshold value;
filtering the inverse differentiated gradient signal in parallel in a second filter stage with a second bipolar filter
filtering said inverse signal in a second the output signals of both second filters are weighted and the weighted output signals are added to a second stimulation signal, which is compared with the first stimulation signal and the maximum of both stimulation signals is used as output signal for comparing with said threshold value.

16. A computer program as claimed in claim 14, wherein said first bipolar filter weights differently stimuli of opposite polarity.

* * * * *